United States Patent [19]

Schlapfer et al.

[11] Patent Number: 5,534,001

[45] Date of Patent: Jul. 9, 1996

[54] OSTEOSYNTHETIC FIXATION ELEMENT AND MANIPULATION DEVICE

[75] Inventors: Johannes F. Schlapfer, Glarus; Robert Frigg, Davos Platz; Thomas Amrein, Horw; Daniel Recher, Hollstein, all of Switzerland; Linda Trebing, Devon, Pa.

[73] Assignee: Synthes (U.S.A.), Paoli, Pa.

[21] Appl. No.: 117,044

[22] PCT Filed: May 11, 1993

[86] PCT No.: PCT/CH93/00118

§ 371 Date: Jul. 15, 1994

§ 102(e) Date: Jul. 15, 1994

[51] Int. Cl.⁶ ................................. A61B 17/56
[52] U.S. Cl. ........................... 606/61; 606/71
[58] Field of Search ................. 606/61, 72, 53, 606/62, 64, 69, 71, 74

[56] References Cited

U.S. PATENT DOCUMENTS

| | | | |
|---|---|---|---|
| 4,611,581 | 9/1986 | Steffee | 606/61 X |
| 4,763,644 | 8/1988 | Webb | 606/61 X |
| 5,181,917 | 1/1993 | Rogozinski | 606/61 |
| 5,263,954 | 11/1993 | Schlapfer et al. | 606/61 |

FOREIGN PATENT DOCUMENTS

| | | |
|---|---|---|
| 0465158 | 1/1992 | European Pat. Off. . |
| 0528177 | 2/1993 | European Pat. Off. . |
| 0535623 | 4/1993 | European Pat. Off. . |
| 2659225 | 9/1991 | France . |

Primary Examiner—Gary Jackson
Assistant Examiner—Nancy Mulcare
Attorney, Agent, or Firm—Fish & Richardson

[57] ABSTRACT

The osteosynthetic fixation element (10) in the form of a pedicular screw or a vertebral column hook has a lower section (2) that can be anchored into a bone and an upper section (3) connected in the direction of its longitudinal axis (1), that is completely penetrated transversely by a penetration channel (8) running transversely to the longitudinal axis (1) for acceptance of a longitudinal support (40). The upper section (3) is provided with an internal threading (5) and an external threading (9) to accept a locking part (30; 50) locking the longitudinal support (40). The upper section (3) is provided at its upper end (6) or at the inserted lock part (30; 50) with a rotationally-stable, releasable connecting mechanism (4, 5, 7; 11, 12) for positive and non-positive temporary acceptance of a manipulation device (20).

15 Claims, 5 Drawing Sheets

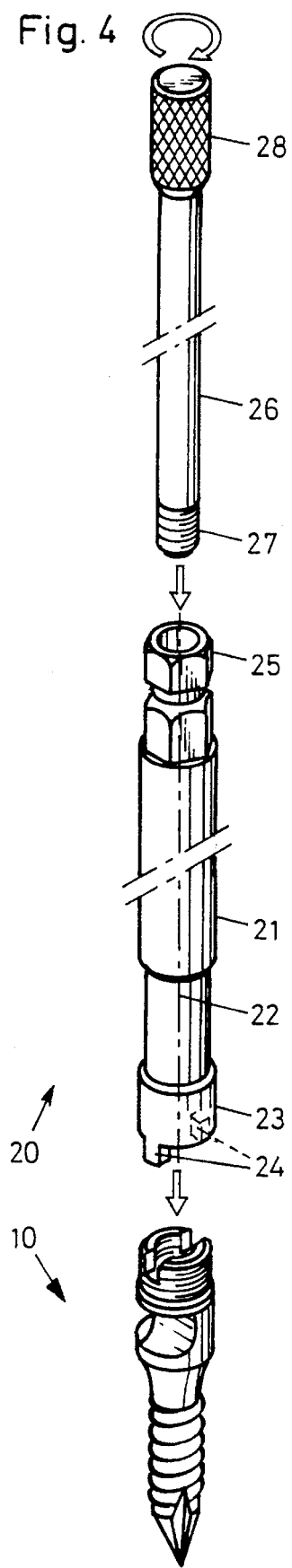
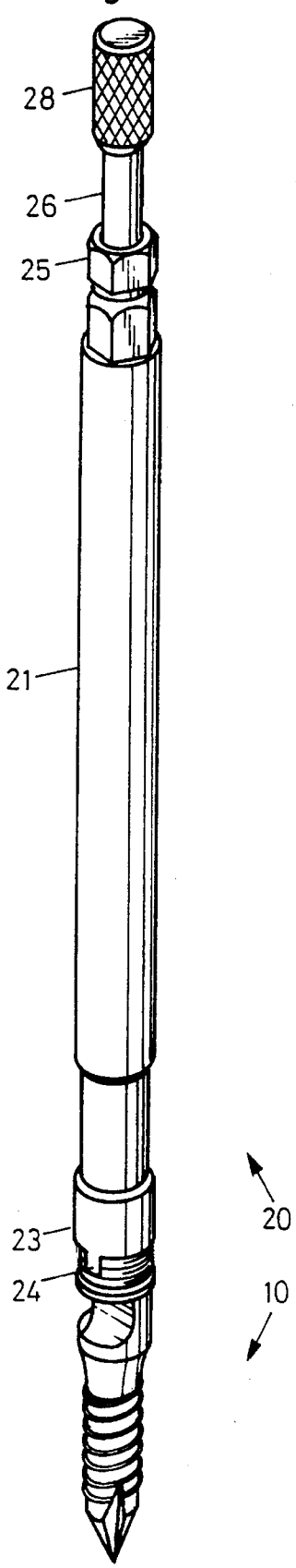
Fig. 4
Fig. 5

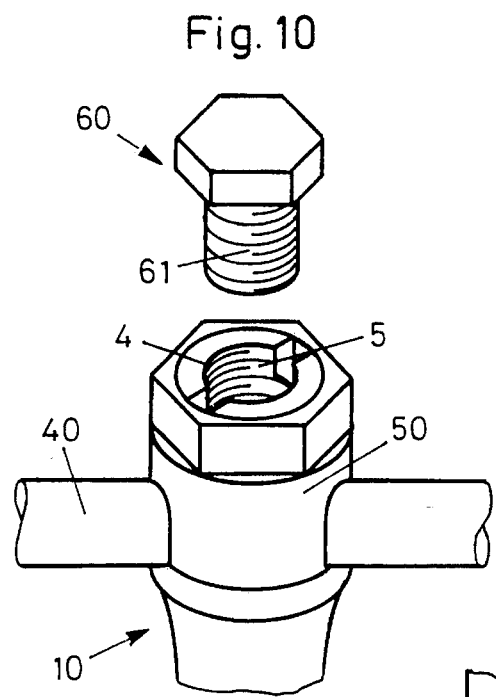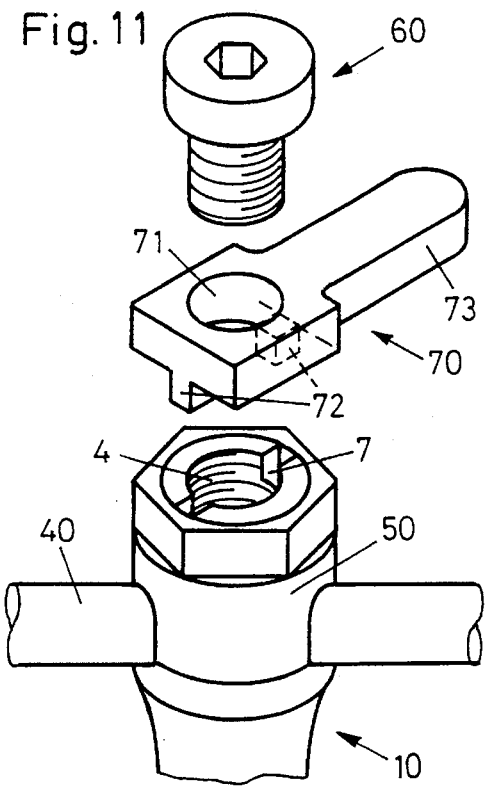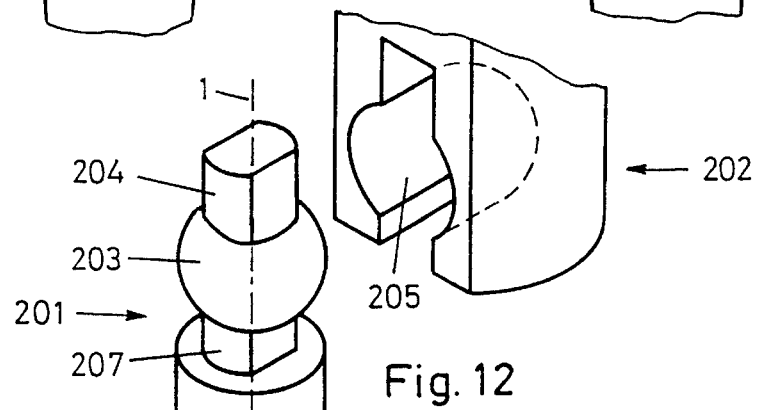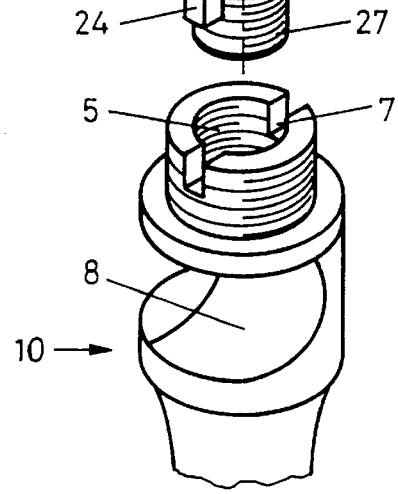

OSTEOSYNTHETIC FIXATION ELEMENT AND MANIPULATION DEVICE

This Application has been filed as a continuation under rule 371 of PCT/CH 93,00118.

The invention refers to an osteosynthetic fixation element, particularly a pedicular screw or a vertebral column hook pursuant to the definition in claim 1 and a device for manipulating the osteosynthetic fixation element.

A fixation element of this type is already known from DE-U1 89.15.443.6, particularly for vertebral column surgery. It consists essentially of a lower portion that can be anchored to the bone, in the form of a screw shaft or a shaft and an upper body, connected thereto, for fastening to a rod, wherein in the body an upward channel opening is created that defines two lateral legs between which the rod can be accepted. The fixation of the rod inside the channel occurs through a threaded plug, the lower end of which, intended for attachment to the rod, is provided with hooks in the form of one or more tips.

The disadvantage in this implantation device is the difficulty in manipulating it when tightening it, which often leads to the longitudinal support not being optimally clamped and over time, pulling out the screw.

The invention is intended to provide assistance here. The invention is directed to the task of creating a fixation element and a device for the manipulation of this osteosynthetic fixation element, which, on the one hand, permits powerful intrasurgical manipulation of the implant and, depending on the embodiment of the implant, offers the opportunity to tighten the fixation element in its position relative to the bone, or to tighten it to other fixation elements, simultaneously with the manipulative process.

The invention solves the task posed with an osteosynthetic fixation element that has the characteristics of claim 1, and a device for the manipulation of the osteosynthetic fixation element that has the characteristics of claim 13.

Further advantageous methods of embodiment are characterized in the subclaims.

The advantages achieved through the invention are to be seen essentially in the fact that it facilitates a powerful insertion and removal motion of the pedicular screws into the vertebral column and hooking and unhooking of the vertebral column hooks. When the pedicular screw is inserted into the bone or the vertebral column hooks are hung, the manipulation device can be used to exert forces and torque via the screws (or the hooks, respectively) on the vertebral column and thus can manipulate deformities. Further advantages lie in the fact that the manipulation device can be removed at any time and remounted and that, via the manipulation device, the implant can be moved in such manner that the longitudinal support can come to lie optimally along the implant.

The invention and additional methods of embodiment of the invention are explained in greater detail below using partial schematic diagrams of several methods of embodiment.

They show:

FIG. 4 is an exploded view of the manipulation device pursuant to the invention;

FIG. 5 is a perspective diagram of the assembled manipulation device pursuant to FIG. 4;

FIGS. 6–12 are perspective diagrams of other methods of embodiment of the fixation element pursuant to the invention;

Figure 1:
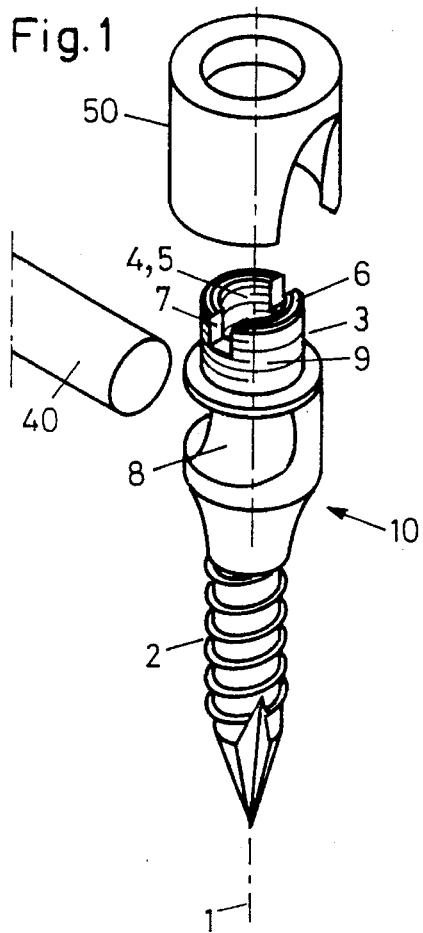
FIG. 1 is a perspective diagram of the osteosynthetic fixation element in the form of a pedicular screw.
Figure 2:
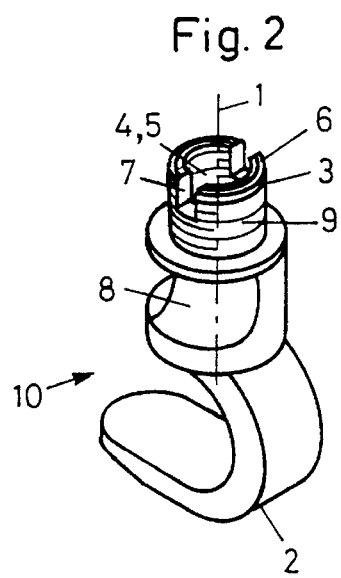
FIG. 2 is a perspective diagram of the osteosynthetic fixation element in the form of a vertebral hook.

Fixation element 10 pursuant to the invention, shown in FIG. 1 or 2 in the form of a pedicular screw or a vertebral hook, consists essentially of lower portion 2 (screw shaft or hook shaft) that can be anchored to the bone, and upper section 3 connecting thereto, in the direction of its longitudinal axis 1, which is completely penetrated by penetration channel 8 running transversely to longitudinal axis 1 for acceptance of longitudinal support 40, and which is provided with external threading 9 to accept lock part 50, locking longitudinal support 40.

Figure 3:
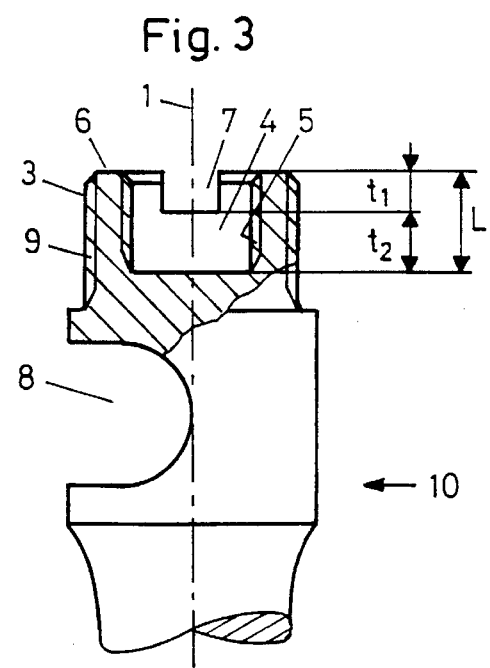
FIG. 3 is a cross-section through the upper portion of the pedicular screw pursuant to FIG. 1.

As shown in FIG. 3, upper section 3 is provided at its upper end 6 with rotationally-stable, releasable connecting mechanism 4, 5, 7 for the temporary positive and non-positive acceptance of manipulation device 20. Connecting mechanism 4, 5, 7 consists of circular cylindrical drill hole 4 opening upward, running in the direction of longitudinal axis 1, provided with internal threading 5, and slit 7 of depth $t_1$ running transversely to longitudinal axis 1, which permits positive acceptance of manipulation device 20 (FIG. 4) with two corresponding lugs 24. Slot 7 serves to provide rotational stability. Internal threading 5 can be designed with multiple threads to strongly shorten the time required for the connection process.

Drill hole 4 with internal threading 5 continues from the base of slot 7 by amount $t_2$ in the direction of lower section 2 for the positive acceptance of manipulation device 20 with corresponding external threading 27 (FIG. 4). Here, drill hole 4 has at least a length $L+t_1+t_2$ and permits a rotationally-stable, releasable connection with manipulation device 20.

Manipulation device 20 shown in FIG. 4 consists of hollow cylindrical sheath 21 with longitudinal axis 22 that has at its one end 23 lug 24 running transversely to longitudinal axis 22. From the other end 25 of sheath 21, cylindrical pin 26 can be inserted into sheath 21. Cylindrical pin 26 carries at its one end external threading 27 that, after successful insertion, protrudes beyond end 23 of sheath 21, and at its other end, grip end 28 protrudes from sheath 21 and serves to tighten the connection.

As shown in FIG. 5, manipulation device 20 coupled to fixation element 10 can be inserted for the transfer of tensile and compressive forces as well as torque to fixation element 10.

Figure 6:
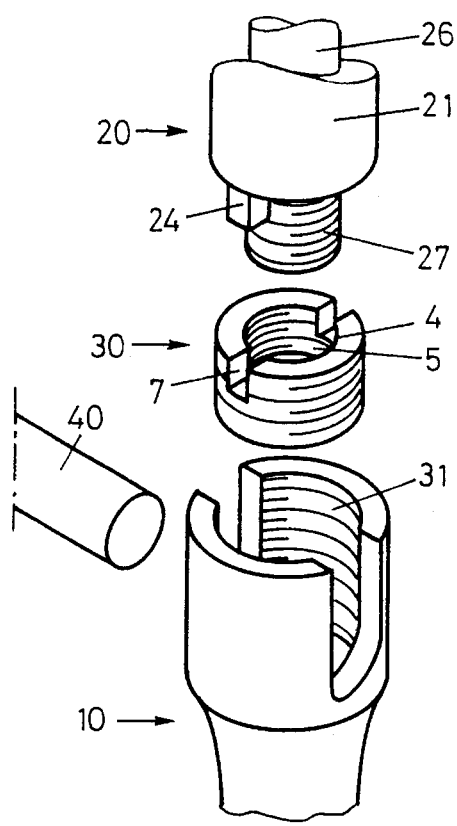

FIG. 6 shows a variation on fixation element 10 in which upper section 3 is designed in two parts in such manner that connecting mechanism 4, 5, 7 consisting of drill hole 4, internal threading 5 and slot 7, is created as lock part 30 formed as a threaded plug, which can be screwed into internal threading 31 of upper section 3. Manipulation device 20 is then coupled with this separate lock part 30 via internal threading 5 to manipulate fixation element 10 and simultaneously to be able to tighten lock part 30 into internal threading 31.

Figure 7:
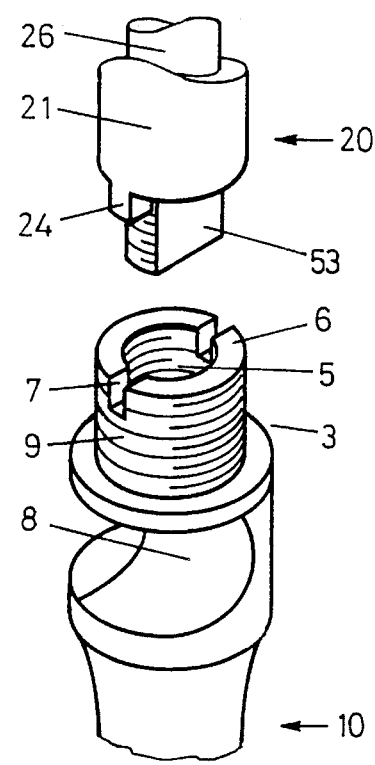

In FIG. 7, an additional variation on the coupling principle between fixation element 10 and manipulation device 20 is shown that functions analogously to a bayonet mount. At the end of pin 26 of manipulation device 20, instead of full threading 27, a bilaterally-flattened threading bolt 53 is provided that rotates 90° after insertion into slot 7 and is thus locked.

Figure 8:
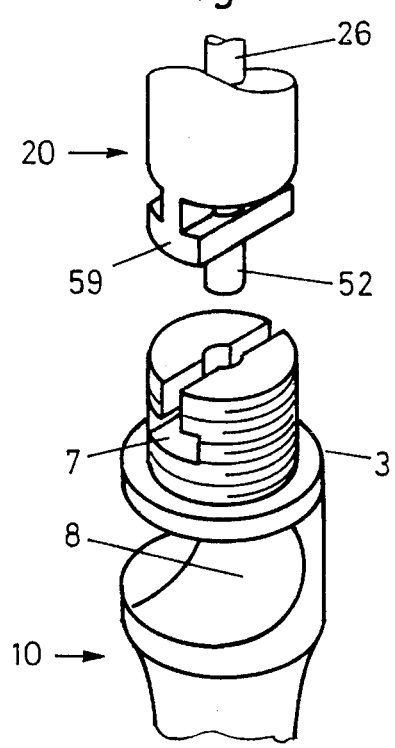

FIG. 8 shows an additional variation on the coupling principle between fixation element 10 and manipulation device 20, where the end of pin 26 of manipulation device 20 is formed as T unit 59 with pin 52. Analogously, slot 7 of fixation element 10 is formed as a T unit. T unit 59 is introduced laterally into slot 7 for coupling and pin 52 is extended downward to prevent sliding out from slot 7. This design principle can also be inverted by forming upper section 3 at its upper end 6 as a T unit and manipulation device 20 instead as a horseshoe.

Figure 9:
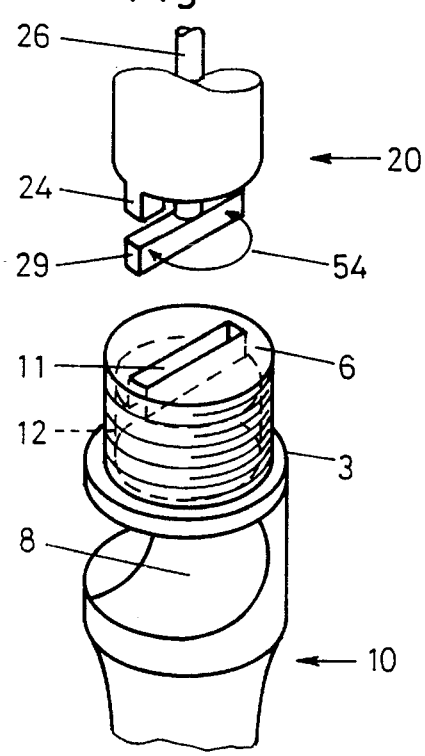

FIG. 9 shows an actual bayonet connection between fixation element 10 and manipulation device 20. At the end of pin 26, T-shaped element 29 is provided and upper end 6 of upper section 3 has slot 11 that expands downward into circular cylindrical hollow 12. T-shaped element 29 can thus be inserted through slot 11 into circular cylindrical hollow 12. Lugs 24 are inserted here merely like a screw driver into slot 11. T-shaped element 29 permits the application of tensile loads and compressive forces on fixation element 10; in the meantime, lugs 24 permit the forward and reverse screwing of fixation device 10 in the direction of arrow 54.

The examples in FIGS. 10 and 11 show the importance in internal threading 5 to the fixation of elements not in direct connection with the manipulation device.

FIG. 10 shows fixation element 10 in which there also is screw 60 with external threading 61 corresponding to internal threading 5, which can be screwed into the area of penetration channel 8 so that longitudinal support can be fixed therewith. In this manner, the solidity of the connection can be increased considerably.

FIG. 11 shows fixation element 10 in which there also is transverse body 70 that has opening 71 corresponding to drill hole 4, two radial lugs 72 corresponding to slot 7, and transverse extension 73 extending radially from opening 71, for connection with other fixation elements 10, and that can be fastened to upper section 3 via screw 60.

FIG. 12 shows a variation on manipulation device 20 that consists of two connectable parts joined to each other, of which the one part 201 includes coupling portion 24, 27, and the other part 202 is a component of another instrument, preferably pincers for repositioning vertebral deformities. The one part 201 has ball-shaped part 203 with cylindrical extension 204 that corresponds to a corresponding lateral opening 205 in the other part 202 of device 20.

Connecting part 207 is bilaterally flattened to avoid rotation of fixation element 10 relative to instrument 202 around longitudinal axis 1 of fixation element 10.

Figure 13:
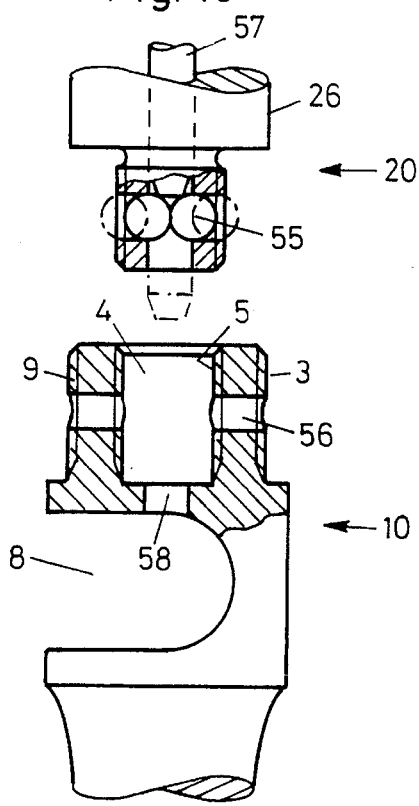
FIG. 13 is a cross-section through the upper portion of a method of embodiment of the fixation element pursuant to the invention and of the lower portion of the manipulation device.

FIG. 13 shows at least one transverse drill hole 56 in upper portion 3 of fixation element 10. Corresponding to this, bearings 55 are provided in pin 26 of manipulation device 20. When manipulation device 20 is introduced into drill hole 4 and bearings 55 square with transverse drill holes 56, pin 57 can be pushed through the central drill hole in manipulation device 20 whereby pin 57 presses bearings 55 into transverse drill holes 56. This facilitates the transfer of tensile, compressive and rotational forces via manipulation device 20. Drill hole 58 serves to accept the pin-like end of safety screw 60.

Figure 14:
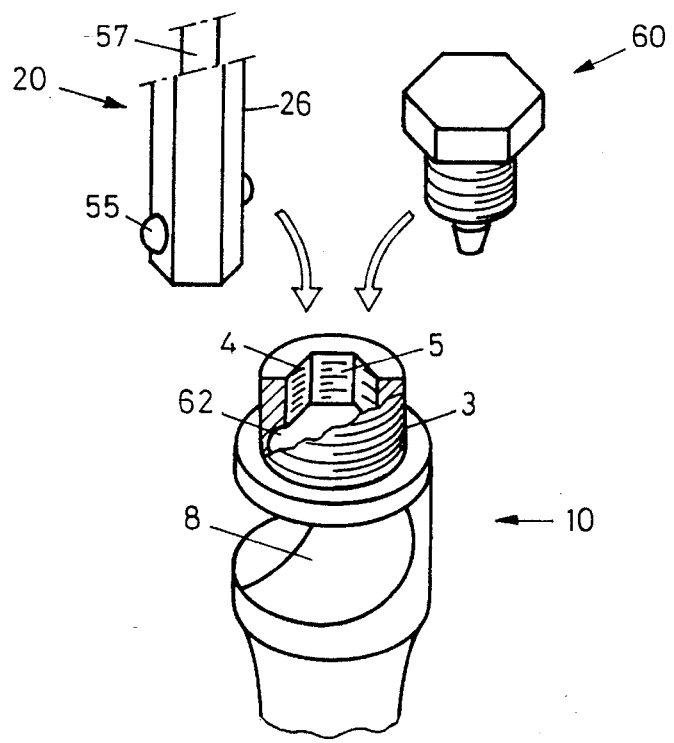
FIG. 14 is a perspective diagram of an additional variation on a fixation element.

Finally, FIG. 14 shows fixation element 10 with drill hole 4 shaped as a hexagon socket and is provided with recess 62 for bearings 55 of manipulation device 20. Bearings 55 are pressed into slot holes 62 via pin 57, analogously to the method of embodiment in FIG. 13. The hexagon socket has on its sides internal threading 5 for fastening additional implants, such as, for instance, safety screw 60.

It is claimed:

1. An osteosynthetic fixation element comprising a shaft having a longitudinal axis, a lower section for attachment to a bone, an upper section having a penetration channel running transversely to said axis to receive a longitudinal support, and a locking part to secure a longitudinal support in said channel, said upper section being threaded to receive said locking part, said upper section further comprising a mechanism for receiving a manipulation device, said mechanism not interfering with said penetration channel and allowing a releasable and a rotational and tension stable connection with said manipulation device.

2. Fixation element according to claim 1, wherein the mechanism of the upper section comprises a bayonet connection.

3. Fixation element according to claim 2, wherein the bayonet connection comprises a slot in the upper section.

4. Fixation element according to claim 1, wherein the penetration channel is placed symmetrically to the longitudinal axis and is open at the upper end of the upper section.

5. Fixation element according to claim 1, wherein:
(a) said mechanism comprises an internally threaded circular cylindrical hole opening upwardly, in the direction of the longitudinal axis;
(b) said mechanism comprises an upper end with a slot of depth $t_1$ running transversely to the longitudinal axis for receiving a manipulation device with lugs adapted to fit into said slot; and
(c) said cylindrical hole extends downwardly from the floor of the slot by an amount $t_2$ in the direction of the lower section, for receiving an externally threaded manipulation device.

6. Fixation element according to claim 5 and comprising a transverse body having an opening corresponding to the cylindrical hole, two radial lugs corresponding to said slot, and a transverse extension extending radially from the opening for connection with other fixation elements.

7. Fixation element according to claim 1, wherein the mechanism comprises a threaded plug.

8. A device for the manipulation of the osteosynthetic fixation element claimed in claim 1, comprising coupling means shaped to engage the mechanism of the fixation element.

9. A device for the manipulation of an osteosynthetic fixation device according to claim 1 and comprising:
(a) a hollow cylindrical sheath having a longitudinal axis and lugs running transversely to the longitudinal axis at a first end; and
(b) a cylindrical pin for insertion into a second end of the sheath, said pin having a first externally threaded end which protrudes beyond the first end of the sheath when said pin is inserted in said sheath, said pin further having gripping means at a second end.

10. The device claimed in claim 9 wherein the sheath comprises coupling means for attachment to a drive mechanism.

11. The device claimed in claim 10, wherein said coupling means has an external thread at one end and a central hole adapted to receive a pin.

12. The device claimed in claim 10, wherein the coupling means comprises a transverse recess, bearings in said recess and a pin in said central hole for urging said bearings out of said recess to a degree such that their overhang, relative to said recess, is less than their diameter.

13. The device claimed in claim 10, wherein said coupling means is polygonal in cross section and has a central hole.

14. The device claimed in claim 10 wherein the coupling means comprises a ball shaped element having a cylindrical extension, for attachment to a drive mechanism having a lateral opening for receiving said ball shaped element.

15. The device claimed in claim 14, wherein the cylindrical extension has flattened portions and the opening in the second part has matching surfaces to prevent relative rotation of the two elements when engaged with one another.

* * * * *